(12) United States Patent
Malhotra et al.

(10) Patent No.: US 12,299,853 B2
(45) Date of Patent: May 13, 2025

(54) DYNAMIC SMOKE REDUCTION IN IMAGES FROM A SURGICAL SYSTEM

(71) Applicant: Verily Life Sciences LLC, South San Francisco, CA (US)

(72) Inventors: Ravish Malhotra, Oakland, CA (US); Kirk Gossage, Pacifica, CA (US)

(73) Assignee: Verily Life Sciences LLC, Dallas, TX (US)

( * ) Notice: Subject to any disclaimer, the term of this patent is extended or adjusted under 35 U.S.C. 154(b) by 440 days.

(21) Appl. No.: 17/966,455

(22) Filed: Oct. 14, 2022

(65) Prior Publication Data
US 2023/0153956 A1 May 18, 2023

Related U.S. Application Data

(60) Provisional application No. 63/278,896, filed on Nov. 12, 2021, provisional application No. 63/295,271, filed on Dec. 30, 2021.

(51) Int. Cl.
*G06T 5/70* (2024.01)
*A61B 1/00* (2006.01)
(Continued)

(52) U.S. Cl.
CPC .......... *G06T 5/70* (2024.01); *A61B 1/000095* (2022.02); *G06T 5/50* (2013.01);
(Continued)

(58) Field of Classification Search
CPC ..... G06T 2207/10056–10136; G06T 5/00–94; G06T 7/90; A61B 1/000095
See application file for complete search history.

(56) References Cited

U.S. PATENT DOCUMENTS 9,288,458 B1 * 3/2016 Chen ......................... G06T 5/50
10,594,931 B2 3/2020 Piponi
(Continued)

FOREIGN PATENT DOCUMENTS

CN 112950488 A * 6/2021 ............. G06T 5/002
WO 2012/112866 A1 8/2012

OTHER PUBLICATIONS

Translation of CN 112950488 (Year: 2021).*
(Continued)

*Primary Examiner* — Sean T Motsinger
(74) *Attorney, Agent, or Firm* — Christensen O'Connor Johnson Kindness PLLC

(57) ABSTRACT

Systems and methods for de-smoking images of a surgical scene are described. Methods include receiving a video of a surgical scene including an image frame. Methods include determining that the image frame includes a smoke occlusion. Methods include determining an estimated un-occluded color of one or more pixels of the image frame using a lookup table, the lookup table mapping between a color space and a set of color bins including the estimated un-occluded color. Methods include determining a respective estimated true color for the one or more pixels of the subset using the imaged color, the estimated un-occluded color, and the smoke color. Methods also include generating a de-smoked image frame using the respective estimated true colors of the one or more pixels, the de-smoked image exhibiting a reduction of the smoke occlusion relative to the image frame.

19 Claims, 8 Drawing Sheets

(51) Int. Cl.
 *G06T 5/50* (2006.01)
 *G06T 7/00* (2017.01)
 *G06T 7/90* (2017.01)
(52) U.S. Cl.
 CPC .............. *G06T 7/0014* (2013.01); *G06T 7/90* (2017.01); *G06T 2207/10016* (2013.01); *G06T 2207/10024* (2013.01); *G06T 2207/10068* (2013.01); *G06T 2207/20192* (2013.01); *G06T 2207/20224* (2013.01); *G06T 2207/30168* (2013.01)

(56) References Cited

U.S. PATENT DOCUMENTS

| | | | |
|---|---|---|---|
| 12,094,035 B2* | 9/2024 | Gubbi Lakshminarasimha | G06T 5/00 |
| 2009/0196476 A1 | 8/2009 | Inoue | |
| 2011/0261261 A1* | 10/2011 | Mori | G06T 5/92 348/E5.077 |
| 2012/0316421 A1 | 12/2012 | Kumar et al. | |
| 2013/0336596 A1* | 12/2013 | Toyoda | G06T 5/20 382/274 |
| 2014/0140619 A1* | 5/2014 | Mukhopadhyay | G06T 5/40 382/167 |
| 2016/0106934 A1 | 4/2016 | Hiraga et al. | |
| 2016/0217346 A1* | 7/2016 | Puetter | G06V 10/56 |
| 2016/0239967 A1* | 8/2016 | Chou | G06T 7/11 |
| 2016/0247276 A1* | 8/2016 | Chou | G06T 7/0012 |
| 2016/0321785 A1 | 11/2016 | Nishimura | |
| 2019/0066336 A1 | 2/2019 | Golde | |
| 2019/0114747 A1* | 4/2019 | Treibitz | G06F 18/22 |
| 2019/0182421 A1* | 6/2019 | Piponi | H04N 1/62 |
| 2020/0177806 A1 | 6/2020 | Piponi | |
| 2020/0202695 A1* | 6/2020 | Ding | G06T 7/251 |
| 2022/0405900 A1* | 12/2022 | Kikuchi | G06T 5/73 |

OTHER PUBLICATIONS

Luo et al., "Vision-Based Surgical Field Defogging," IEEE Transactions on Medical Imaging, vol. 36, No. 10, Oct. 2017, pp. 2021-2030.

Nishino et al., "Bayesian Defogging," Int. J. Comput. Vis., 2012, vol. 98, pp. 263-278.

Tchaka et al., "Chromaticity Based Smoke Removal in Endoscopic Images," Medical Imaging 2017: Image Processing, Proceedings of SPIE, vol. 10133, 10 pages.

Photoshop Lightroom Classic CC, "Remove Haze with Dehaze Feature in Lightroom", retrieved from internet <https://helpx.adobe.com/lightroom/how-to-remove-haze-dehaze.html> on Oct. 22, 2017, 4 pages.

Berman et al., Non-Local Image Dehazing, Proceedings of the IEEE Conference on Computer Vision and Pattern Recognition (CVPR), 2016, pp. 1674-1682.

Eisen-Enosh et al., Evaluation of Critical Flicker-Fusion Frequency Measurement Methods for the Investigation of Visual Temporal Resolution, www.nature.com/scientificreports, Nov. 15, 2017, 9 pages.

International Search Report and Written Opinion, issued Mar. 3, 2023, in corresponding International Patent Application No. PCT/US2022/47606, 11 pages.

* cited by examiner

DYNAMIC SMOKE REDUCTION IN IMAGES FROM A SURGICAL SYSTEM

CROSS REFERENCE TO RELATED APPLICATIONS

This application claims the benefit of priority to U.S. Provisional Application No. 63/278,896, filed on Nov. 12, 2021, and to U.S. Provisional Application No. 63/295,271, filed on Dec. 30, 2021, the contents of each of which are incorporated by reference herein in their entireties.

TECHNICAL FIELD

This disclosure relates generally to processing of images from surgical systems, and in particular but not exclusively, relates to a system and method for reducing smoke occlusion in endoscope images.

BACKGROUND INFORMATION

In recent years, computer-assisted surgery has become a popular way to overcome limitations of existing surgical procedures, and possibly enhance the capabilities of doctors performing the surgery. For example, without computerized equipment, doctors can be limited to where they can operate/examine due to the size of their hands and limited dexterity with tools. This inhibits the ability of doctors to operate on small or deep internal tissues.

In open surgery, for example, computer-guided instruments can replace traditional (hand-held) tools to perform operations such as rib spreading due to the smoother feedback assisted motions of computer-guided instruments. Robotic systems like this have been shown to reduce or eliminate tissue trauma commonly associated with invasive surgery. Moreover, these instruments can reduce the likelihood of error by detecting and/or preventing accidental mistakes during surgery.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
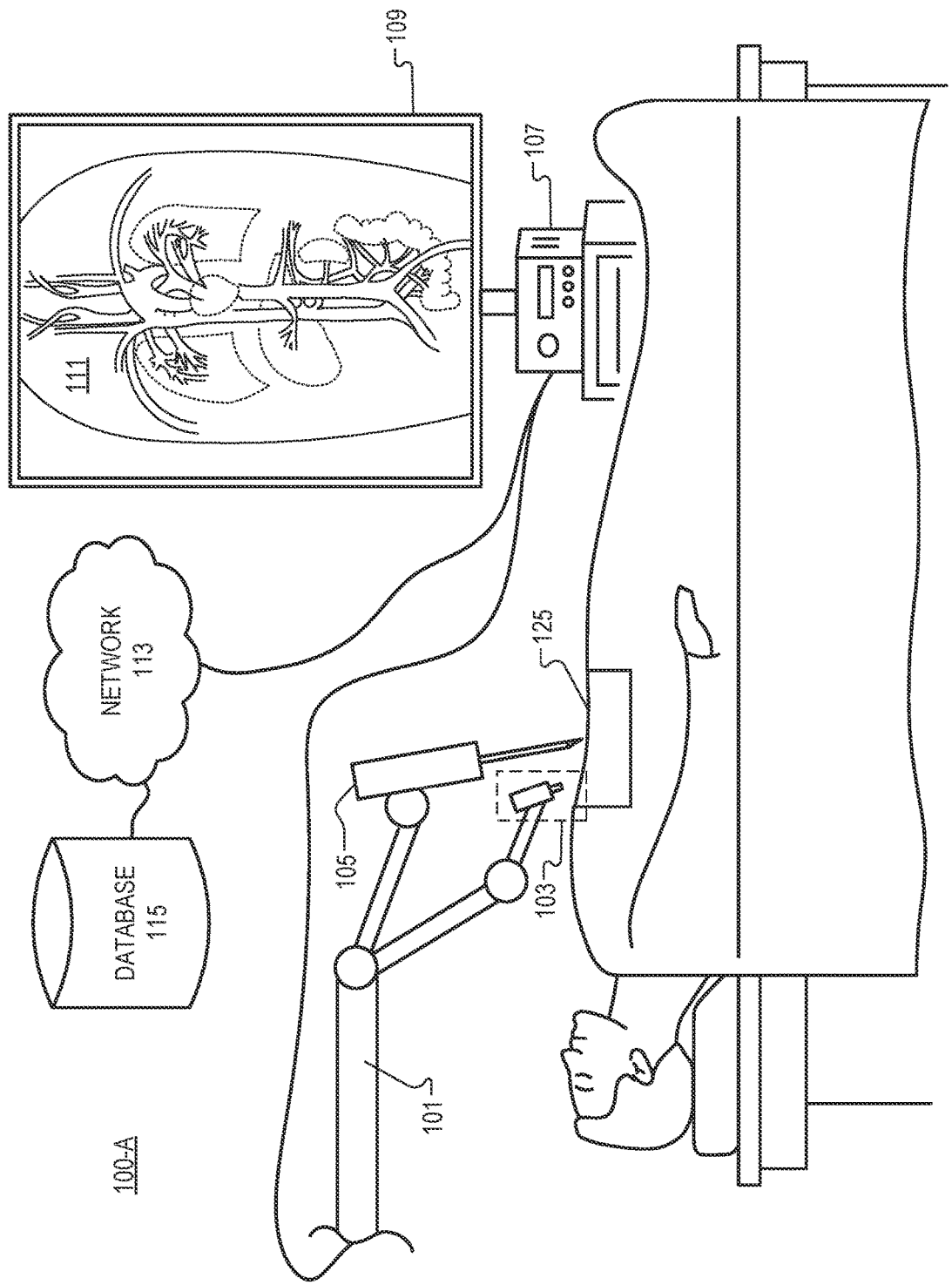
FIG. 1A is an example surgical system for outputting images with reduced smoke occlusion, in accordance with an embodiment of the disclosure.

Embodiments of a system and a method for reducing smoke occlusion in video image frames from surgical systems are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "selecting", "identifying", "capturing", "adjusting", "analyzing", "determining", "estimating", "generating", "comparing", "modifying", "receiving", "providing", "displaying", "interpolating", "outputting", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such as information storage, transmission, or display devices.

The algorithms and displays presented herein are not inherently related to any particular computer or other apparatus. Various general-purpose systems can be used with programs in accordance with the teachings herein, or it can prove convenient to construct a more specialized apparatus to perform the required method steps. The required structure for a variety of these systems will appear from the description below. In addition, embodiments of the present disclosure are not described with reference to any particular programming language. It will be appreciated that a variety of programming languages can be used to implement the teachings of the disclosure as described herein.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

Cauterization is a surgical technique of burning tissue to cut through, remove, or seal the tissue while mitigating bleeding and damage. Cauterization devices such as an electrocautery knife, a harmonic scalpel, a laser scalpel, or the like allow a surgeon to perform cauterization at precise locations during a surgical procedure. However, surgical smoke can be released as a by-product of burning the tissue desired to be cut, sealed, or removed. In general, surgical smoke can be described as a particulate and/or vapor byproduct produced by electrosurgery, laser tissue ablation, ultrasonic scalpel dissection, high speed drilling or burring, or any procedure done by means of a surgical instrument that is used to ablate, cut, coagulate, desiccate, fulgurate, or vaporize tissue.

During certain situations, the surgical smoke can cause a smoke occlusion that obstructs a surgeon's view of the surgical site and potentially prevents further progress of the surgical procedure until the smoke occlusion is reduced or removed. One way of reducing the surgical smoke causing the smoke occlusion is to periodically release or evacuate the surgical smoke from the surgical site. For example, during laparoscopic surgery small incisions are made within the abdomen to allow for the insertion of surgical instruments such as an endoscope and a cutting instrument (e.g., a harmonic scalpel). The abdomen is then sealed and filled with carbon dioxide using a gas plenum integrated into the endoscope to elevate the abdominal wall above the internal organs to create a working and viewing spacing. The use of the cutting instrument can generate surgical smoke within the sealed abdominal cavity, which can create a smoke occlusion that interferes with the surgeon's view of the surgical site. Periodically, the surgeon can halt progress of the surgical procedure to have surgical staff physically evacuate the surgical site of surgical smoke with a vacuum or the like and then refill the surgical site with carbon dioxide. However, in some situations, evacuation can interrupt, distract, or otherwise disrupt the surgeon from performing the surgical procedure. Moreover, there can be time critical periods during which halting the surgical procedure is not an option.

Described herein are embodiments of a system and a method for reducing or substantially eliminating smoke occlusion in images from surgical systems. The described embodiments can be both an alternative and/or complementary approach to physically evacuating surgical smoke from a surgical site. In particular, the described embodiments utilize image processing to reduce or substantially eliminate the appearance of the smoke occlusion caused by the surgical smoke in images/videos of the surgical procedure in near-real time.

In this context, the term "near-real time" is used to indicate that a nonzero latency can be introduced by image processing operations described herein that are imperceptible to human operators of surgical systems and/or viewers of video streams including de-smoked images. In an illustrative example, video streams described herein can be generated by endoscopes or other camera devices at a rate of about 24 Hz (41.7 msec), about 30 Hz (33.3 msec), about 60 Hz (16.6 msec), about 120 Hz (8.3 msec), or other framerates, for which the corresponding period in milliseconds per frame is quoted in parentheses. Advantageously, the processes described herein can be configured to introduce latency of about 5 msec or less, about 4 msec or less, about 3 msec or less, 2 msec or less, 1 msec or less, or less, including interpolations and fractions thereof. As would be understood by a person having ordinary skill in the art, sensitivity of human vision to motion in an image or video stream begins to plateau at a period of approximately 76.9 msec, corresponding to a framerate of 13 Hz, and a critical flicker frequency above which flickering in a motion picture or video becomes imperceptible to most viewers occurs at about 25 Hz to 40 Hz (25 msec to 40 msec), such that a latency from about 1 msec to about 5 msec added for a subset of frames in a video is likely to be imperceptible to most viewers.

Advantageously, the techniques described herein can be applied to a variety of surgical camera systems in a "scope-agnostic" manner. In this context, "scope-agnostic" refers to the capability of image processing systems described herein to be integrated with existing surgical imaging systems without calibration or other adaptation to optical, hardware, and/or software configurations of the respective systems. In this way, a computer system (e.g., software and/or software implemented in hardware) configured to implement de-smoking processes described herein can be configured to receive data from an imaging device (e.g., camera, scope, etc.) in a "plug and play" manner, and can thus be introduced between the imaging device and a display used by a surgeon to visualize a surgical scene to process frames of a video and to reduce and/or substantially remove smoke from one or more frames. In an illustrative embodiment, software implementing the techniques herein can be integrated into an endoscope device that includes image processing software and hardware for executing the software, such that the images generated by the endoscope camera are processed for de-smoking before being sent to a display.

FIG. 1A is an example surgical system 100-A that outputs images with reduced smoke occlusion, in accordance with an embodiment of the disclosure. Surgical system 100-A includes a surgical robot 101, an image sensor 103 (e.g. a video camera), a surgical instrument 105 (e.g., a cauterizing instrument, such as an electrocautery knife, a harmonic scalpel, a laser scalpel, or any other surgical instrument that can cause surgical smoke to be released upon use), a controller 107 (e.g., a computer system which may, in some embodiments, include a processor and memory/storage), a display screen 109 (displaying a de-smoked image frame 111 of a surgical site that has been processed, in near-real time, to have a reduced amount of a smoke occlusion caused by surgical smoke), and a database 115 (coupled with computer 107 wired or wirelessly via a network 113).

Image sensor 103 is positioned to capture a video of a surgical scene 125 while a surgical procedure is performed with surgical system 100-A. The video captured during the surgical procedure by image sensor 103 includes an image frame representing a view of the surgical site and includes tissue that is at least partially occluded by a smoke occlusion due to surgical smoke. The surgical smoke can be a by-product produced during a use or activation of surgical instrument 105 (e.g., cauterization of tissue with a harmonic scalpel during a cauterization event). Without being bound to a particular physical phenomenon, surgical smoke can be an absorbing/scattering medium, rather than a reflective medium, based on the average particle size of smoke particles or droplets. In this way, the image frame includes a plurality of pixels each having an imaged color captured by image sensor 103, where the imaged color represents a convex combination of the color of a body tissue in surgical scene 125 and a color of the smoke in surgical scene 125. In this context, the term "convex combination" is used to refer to a linear combination of points (which can be vectors, scalars, or more generally points in an affine space) where all coefficients are non-negative and sum to one, representing the imaged color of a given pixel.

Smoke inside a body cavity that is generated during surgery can act like other volumetric scattering media, such as haze or fog, which can have a path-length dependent scattering effect that reduces the intensity of diffuse reflected light and increases the intensity of scattered light with increasing path length through the smoke. As such, surfaces farther from the viewer (e.g., an endoscope) can appear closer to the color of smoke and surfaces nearer to the viewer will appear closer to the color of the tissue surface. In contrast to volumetric scattering media where the volumetric distribution is uniform, however, regions of surgical scenes 125 that appear closer to the color of smoke can have a higher smoke density as a result of proximity to a cauterization site that acts as a point source of smoke. De-smoking image frames, therefore, involves determining a relative contribution in color space from an estimated true color of the surface and a color of smoke that is based at least in part on local smoke density, rather than the distance of the surface from the viewer.

Controller 107 is coupled with image sensor 103 to receive the video, including the image frame. Controller 107 can be a computer system (e.g., one or more processors coupled with memory), an application specific integrated circuit (ASIC), a field-programmable gate array, or the like, configured to coordinate and/or control, at least in part, operations of surgical system 100-A. Stored on controller 107 (e.g., on the memory coupled with controller 107 or as application specific logic and associated circuitry) are instructions that, when executed by controller 107, causes surgical system 100-A to perform operations for determining smoke-occluded image frames and/or de-smoking image frames. The operations include determining an estimated true color of at least a subset of the pixels in the image frame based, at least in part, on the imaged color. The estimated true color is closer to an un-occluded color of the tissue than the imaged color by reducing or substantially eliminating haze, smoke, or other shifts in the color of at least some of the pixels making up the image frame in a color space that includes the un-occluded colors of surgical scene 125 (e.g., the body cavity). In this context, the term "color" is used to describe tuple of color coordinates in a color space that defines each color as a combination of multiple color components. An example for additive color is an RGB color space where each color can be expressed as an additive combination of three different color coordinates. An example for subtractive color is a CMYK color space where each color can be expressed as a subtractive combination of four different color coordinates. For lit-display systems, as in many digital video displays, additive color, such as RGB, is typically used. In e-paper or other unlit displays, subtractive color, such as CMYK, is typically used.

A de-smoked image frame 111 with a reduced or substantially negligible extent of smoke occlusion relative to the first frame is then generated, at least in part, by controller 107 based on the determined estimated true color of each of the plurality of pixels. This process can continue for each image frame of the video (e.g., the video can include a plurality of image frames, including the image frame) to generate a de-smoked video (including the de-smoked image frame 111) that is subsequently output to display screen 109 in near-near-real time.

Thus, while capturing the video of the surgical procedure, controller 107 can continuously and in near-real time de-smoke (e.g., reduce or substantially remove the smoke occlusion) the video to generate the de-smoked video and subsequently output the de-smoked video to display screen 109. This can allow the surgeon to perform a surgical procedure (e.g., endoscopic surgery) with fewer pauses or halts since it cannot be necessary to physically evacuate surgical smoke as frequently, if at all. Moreover, the generation of the de-smoked video in near-real time can allow the surgeon to more clearly view the tissue while performing a surgical technique that generates the surgical smoke as a by-product.

In the depicted embodiment, image sensor 103 is directly coupled (wired) to controller 107, but in other embodiments, there can be intervening pieces of circuitry and controller 107 can be indirectly coupled (wireless) to image sensor 103. Similarly, in some embodiments, controller 107 can be part of a distributed system (e.g., many processors and memory units can be used in the calculations to handle processing). Additionally, database 115 is illustrated as directly coupled (wired) to controller 107 through network 113. However, it is appreciated that in some embodiments, controller 107 can be indirectly coupled (wireless) to network 113 and/or database 115. Database 115 can be a surgical video database coupled with controller 107.

As illustrated, only a portion of surgical robot 101 is shown and not to scale, with some components omitted for simplicity of visual explanation. Surgical robot 101 is shown as having two arms, each respectively holding image sensor 103 and surgical instrument 105. However, surgical robot 101 can have any number of arms with a variety of surgical instruments (e.g., clamps, tweezers, etc.). As shown, the arms can have a number of joints with multiple degrees of freedom so that surgical system 100-A can move freely with as many, or more, degrees of freedom as the surgeon. Additionally or alternatively, surgical robot 101 can provide haptic feedback to the surgeon by way of pressure, strain, and/or stress sensors disposed within the arms or surgical instruments of surgical robot 101. Furthermore, a plurality of image sensors 103 can be used to form the video and corresponding plurality of image frames. Individual images captured by the plurality of image sensors 103 can be combined by surgical system 100-A to seamlessly generate image frames from two or more image sensors.

Figure 1B:
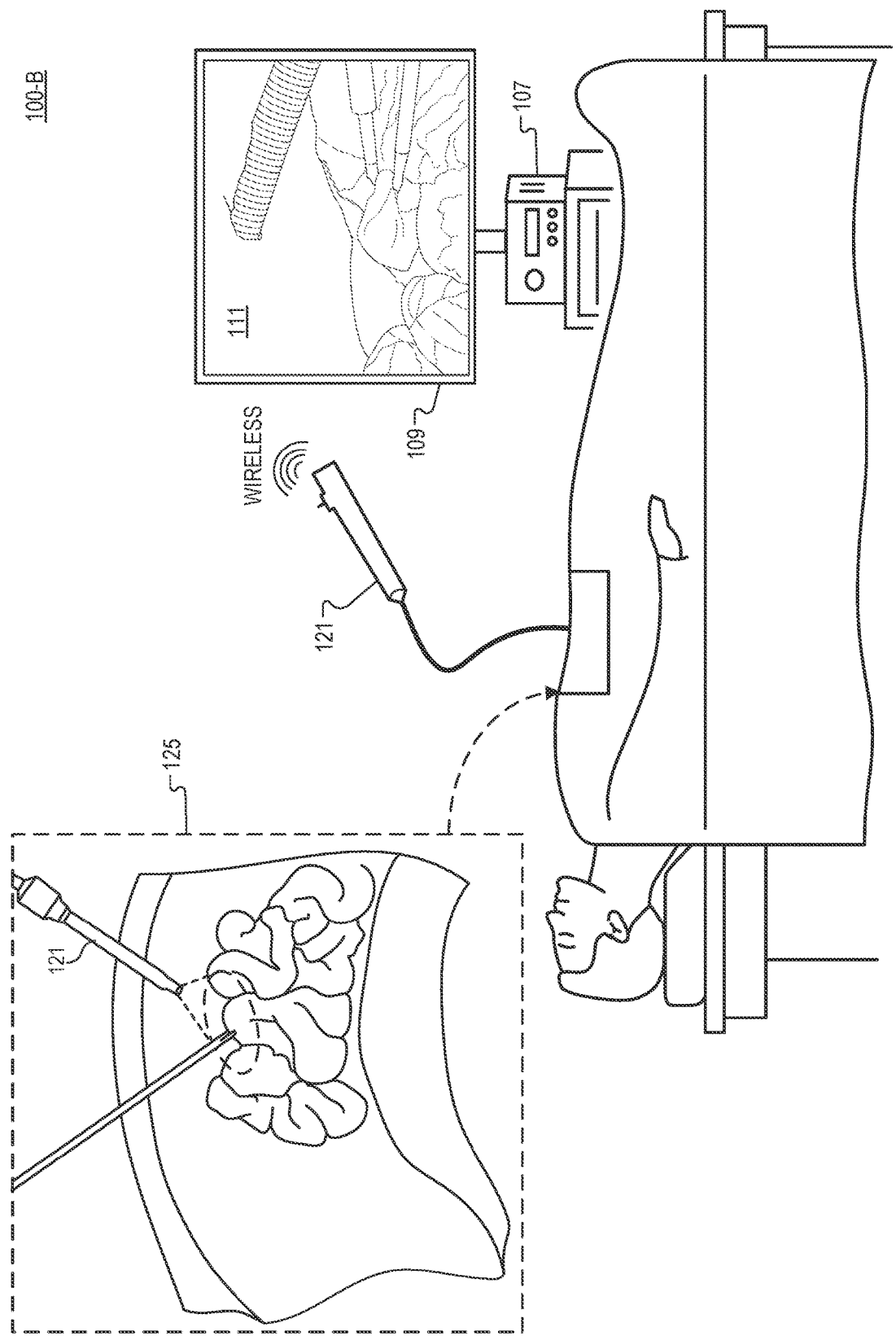
FIG. 1B is an example surgical system for outputting images with reduced smoke occlusion, in accordance with an embodiment of the disclosure.

FIG. 1B is an example surgical system 100-B for outputting images with reduced smoke occlusion, in accordance with an embodiment of the disclosure. Surgical system 100-B includes an endoscope 107 (e.g., a laparoscope, a bronchoscope, a cystoscope, a colonoscope, a sigmoidoscope, a thoracoscope, a laryngoscope, an angioscope, an arthroscope, or the like) in addition to or instead of the surgical robot 101 to generate video of surgical scene 125. In some embodiments, endoscope 121 can wirelessly transfer video streams (including the image frame) to controller 107 in near-real time according to a framerate. Endoscope 121 can be inserted into the patient (as shown) through small incisions to view and operate on the internal organs or vessels of the patient (e.g., to view the anatomical location and/or perform the surgical procedure). Surgical system 100-B illustrates the output to display screen 109 the de-smoked image frame 111. Furthermore, it is appreciated that surgical system 100-B illustrates the systems and methods disclosed herein are compatible with a variety of surgical procedures and surgical instruments, as one of ordinary skill in the art will appreciate.

Figure 2:
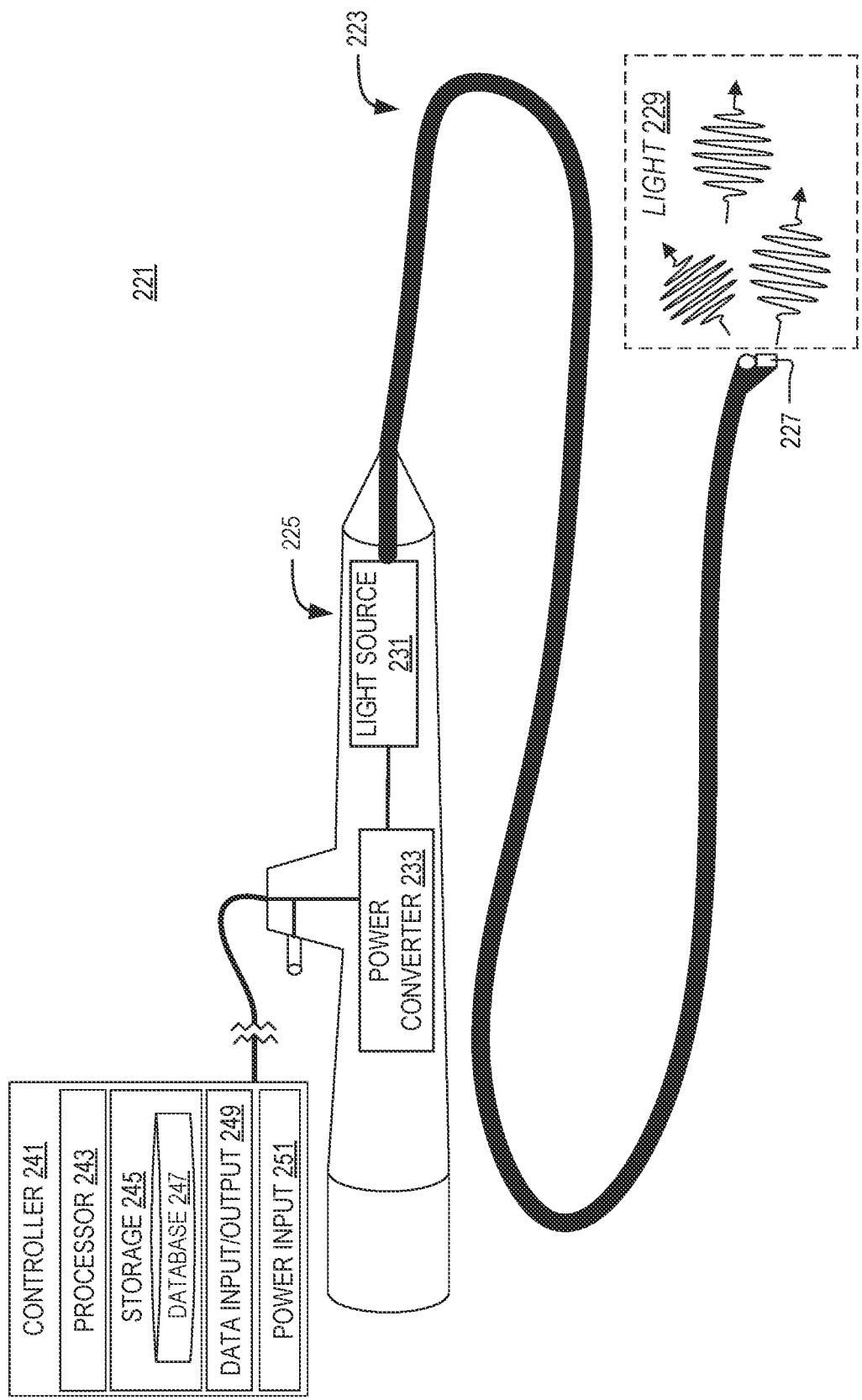
FIG. 2 is an example endoscope which can be used in the surgical system of FIG. 1B, in accordance with an embodiment of the disclosure.

FIG. 2 is an example endoscope 221 which can be used in the surgical system of FIG. 1B, in accordance with an embodiment of the disclosure. Endoscope 221 is one possible implementation of endoscope 121 of FIG. 1B. Referring back to FIG. 2, endoscope 221 includes a fiber optic cable 223, a housing 225, an image sensor 227, a light source 231, and a power converter 233. In some embodiments, endoscope 221 can be implemented as part of a remote surgery system (e.g., system 100A of FIG. 1A).

Endoscope 221 includes a proximal end (to be hand-held or mounted) and a distal end (end of fiber optic cable 223 closest to image sensor 227) to be inserted into a patient receiving the surgical procedure. Light source 231 is optically coupled with the proximal end of fiber optic cable 223 to emit visible light 229 into fiber optic cable 223 for output from the distal end. The distal end is positioned within the patient and illuminates the surgical site. Image sensor 227 is coupled with the distal end of fiber optic cable 223 and positioned to receive a reflection of visible light 229 that illuminates the surgical site to capture the video (including the image frame) of the surgical procedure.

Controller 241 is similar in many regards to controller 107 of the surgical system of FIG. 1A and can include the same components and functionality. Referring back to FIG. 2, controller 241 can be disposed internal (e.g., disposed with housing 225) or external (e.g., wired or wirelessly connected) to endoscope 221. Controller 241 includes a processor 243, storage 245 (e.g., any computer-readable storage medium) with database 247, data input/output 249 (e.g., to send/receive the video from image sensor 227), and power input 251 (e.g., to power endoscope 221). Data input/output 249 can include an input apparatus coupled with controller 241. The input apparatus can be positioned to receive an input command from an operator (e.g., the surgeon). In response to receiving the input command, the surgical system can adjust a level-parameter of de-smoking operations in line with an expected smoke occlusion or in response to generating smoke. The level-parameter can describe a binary on-off state of de-smoking or can be incremental to adjust an extent of de-smoking (e.g., a continuous variable between "off" and "on"). In some embodiments, the surgeon can manually adjust the amount of the smoke occlusion that is reduced or removed. In some embodiments, a linear interpolation of the plurality of image frames compared to the de-smoked plurality of image frames can be used to adjust the amount the smoke occlusion is reduced or removed. For example, linear interpolation of the image frame and the de-smoked image frame can allow for controlling the amount of the smoke occlusion.

Figure 3:
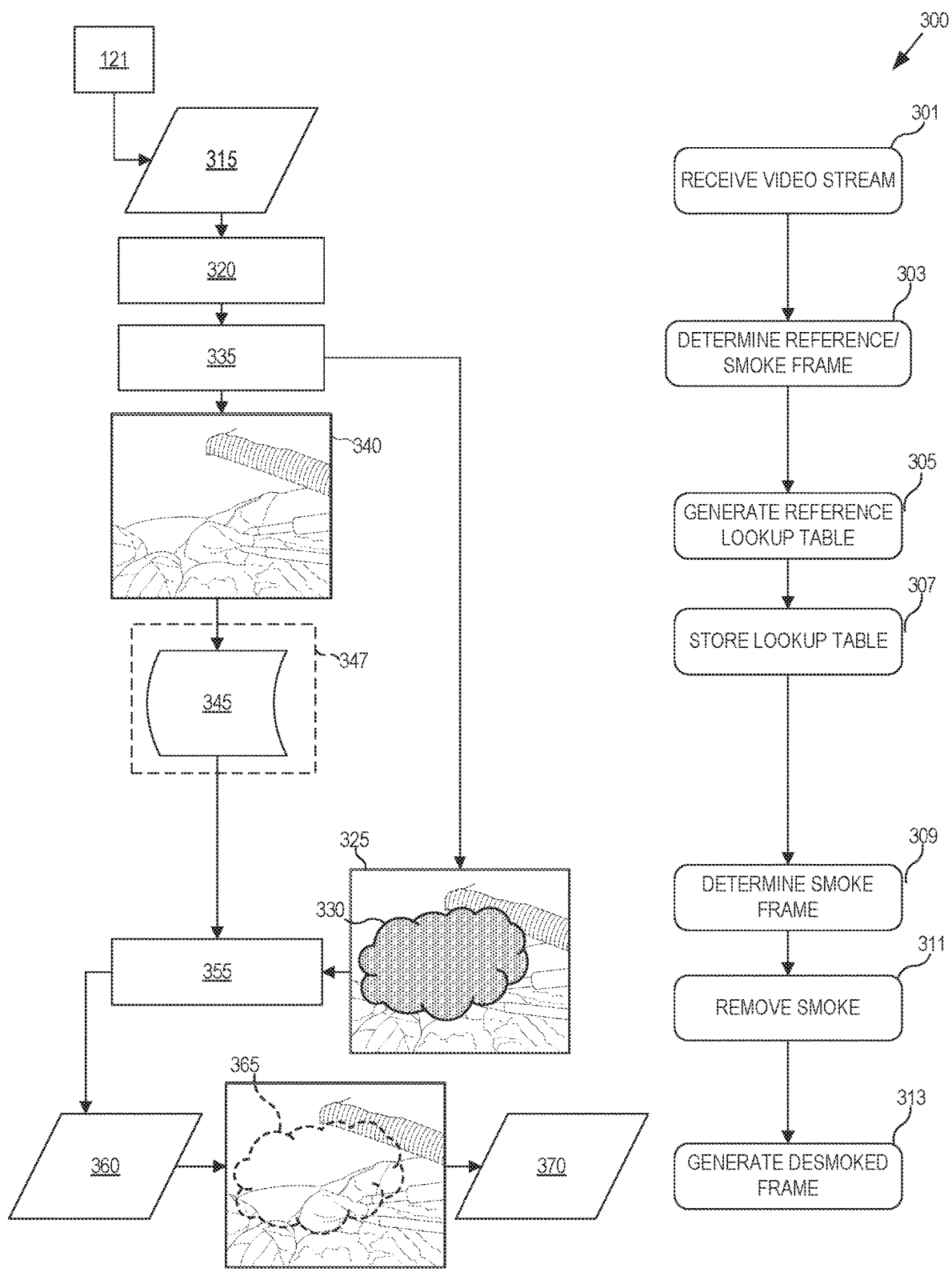
FIG. 3 is a schematic diagram illustrating an example process for reducing and/or substantially eliminating a smoke occlusion in one or more image frames of a video depicting a surgical scene, in accordance with embodiments of the disclosure.

FIG. 3 is a schematic diagram illustrating an example process 300 for reducing and/or substantially eliminating a smoke occlusion in one or more image frames of a video depicting a surgical scene, in accordance with embodiments of the disclosure. Example process 300 describes a sequence of operations that can implemented by various hardware elements, including, but not limited to the embodiments of surgical system 100-A of FIG. 1A and surgical system 100-B of FIG. 1B. In particular, a controller (e.g., controller 107 of FIG. 1A, controller 107 of FIG. 1B, or controller 241 of FIG. 2) can include instructions (e.g., stored on memory) or logic (e.g., an application specific integrated circuit) for performing example process 300. Additionally, or alternatively, example process 300 can be implemented as instructions stored on any form of a non-transitory machine-readable storage medium. In some embodiments, one or more of operations 301-311 of example process 300 can be omitted, repeated, reordered, or executed concurrently (e.g., by parallelization), rather than in sequence as illustrated.

Example process 300 describes a technique for improving imaging during the surgical procedure in near-real time by reducing and/or substantially eliminating the appearance of smoke occlusion in a surgical scene. Additionally or alternatively, the constituent operations of example process 300 can be applied to smoke-occluded surgical video files for post-operative analysis, as opposed to buffered near-real time video streams. Description of constituent operations making up example process 300 are of operations 301-311 focuses on operations applied to video data 315, with examples of the computational processes applied as part of the operations explained in detail in reference to FIGS. 4A-5.

In this context, a smoke color refers to the perceived color of surgical smoke generated by scattering of visible and ultraviolet light by smoke particulates. The smoke color is typically a whitish color, owing to smoke acting as a wavelength-uniform scattering medium, which can cause a smoke occlusion that at least partially obstruct a surgeon's view of a surgical site. A person of ordinary skill in the relevant art would recognize that smoke color is another term for "airlight," which is a term describing the perceived color of smoke, haze, fog, or other scattering media that is used in technical descriptions of de-hazing techniques in wide-angle still images of landscapes and other scenes depicting relatively large distances. As previously described, images of a surgical scene that includes smoke will include light reflected from the body cavity or other biological surface in surgical scene 125 and light that has been scattered by the smoke. To that end, an imaged color represented in image frames of a video will be a convex combination of the un-occluded color of the surface and the smoke color.

In some embodiments, example process 300 includes receiving a video 315 of a surgical scene, including multiple image frames 320 and 325, at operation 301. As described in more detail in reference to FIGS. 1A-2, operation 301 can include operatively coupling a computing device configured to implement example process 300 between the camera and/or scope and the display. In this way, image frames 320 can be received as a buffered stream of image data, as a sequence of image files, or the like, as would be understood by a person having ordinary skill in the relevant art. Image frames 320 represent a snapshot generated by the image sensor 121 using multiple sensor pixels, according to the resolution of the sensor. Image frames 320 can be compressed, filtered, or otherwise adjusted prior to operation 301 or can be received at native resolution and as generated by the image sensor. Advantageously, example process 300 can be agnostic to such prior image processing operations by referencing de-smoking operations using image frames 320 without smoke 330.

Image frames 320 can include one or more image frames 320 that are free of smoke 330 and one or more image frames 320 with smoke occlusion 325. Image frames 320 include pixels having a respective imaged color that together represent the body cavity and/or body tissue making up surgical scene 125. At least a subset of the pixels in an image frame including smoke 330 are affected by the smoke occlusion. As defined by a given surgical system (e.g., surgical system 100-B of FIG. 1B), the color value of a pixel can be defined by coordinates in the RGB color space. In some embodiments, eight-bit precision is used which allows for R (red), G (green), and B (blue) coordinates between zero and two hundred and fifty five. In this illustrative example a pixel can describe, through a tuple of color values, 16,777,216 different colors. Advantageously, techniques described herein reduce the computational resource demand of processing the range of colors in a true-color image and reduces the latency introduced by processing time with the full color range, at least in part by quantizing images into a subset of colors. In this way, example process 300 improves the performance of computer systems used for de-smoking images in video, and improves the experience of a user (e.g., a surgeon) of the system in viewing a de-smoked scene with reduced latency.

In some embodiments, an image processing pipeline can include one or more optical and/or signal filters/corrections (e.g., a gamma correction) that are applied to the color value of the pixels included in image frames 320. Advantageously, the constituent operations of example process 300 can be applied in a scope-agnostic manner, by basing de-smoking modifications at least in part on reference frames 340 received from the same system and under the same system condition. In this way, example process 300 can be implemented in a variety of surgical systems (e.g., surgical system 100A or 100B of FIGS. 1A-1B) that implement different hardware and software for imaging surgical scene 125. In some embodiments, the implementation can be achieved without additional calibration or adjustment, in a "plug and play" manner. In some cases when imaging systems apply dynamic correction to account for changes in average luminance of a surgical scene for example, example process 300 can adapt to such changes by defining new reference frames 340.

In some embodiments, example process 300 includes determining that video 315 includes reference frame 340 at operation 303. As previously described, reference frame 340 is an image frame of video 315 that depicts surgical scene 125 but does not include smoke 330. In some embodiments, operation 303 includes generating an average luminance of the plurality of pixels of the image frame. To limit processing to image frames 320 including meaningful information about surgical scene 125, luminance thresholding can be used as a first pass to exclude frames that are too bright or too dark to be effectively processed. Luminance can be defined as a value from zero to one, such that the luminance thresholding can be applied to process images having an average luminance from about 0.1-0.9, about 0.2-0.8, about 0.3-0.7, about 0.4-0.6, about 0.3-0.5, or the like. With a narrower luminance range, fewer image frames 320 are processed, which can improve latency and reduce computational resource demand, but can also impair the efficacy of example process 300 to define luminance thresholds to exclude a significant number of frames. In this way, luminance thresholding can be used to exclude image frames 320 that would be too bright or too dark for the user to interpret accurately.

In some embodiments, operation 303 includes one or more suboperations to determine whether the image frame depicts surgical scene 125. Suboperations can include processing image frame 320 using a machine learning model, such as a deep-convolutional neural network trained to classify images as surgical scene 125 images or non-surgical scene images. In some embodiments, suboperations include generating a set of principal color components of the image frame and generating a comparison of the set of principal color components to a reference set of principal color components of a biological surface.

The comparison can be or include a statistical analysis of color distributions by populating a color histogram for image frame 320 and comparing it to a reference color histogram (e.g., by an analysis of variance test) and/or by comparing principal colors to each other to determine whether the video 315 is depicting surgical scene 125. In this way, operation 303 can include a determination to process the image frame where the comparison between the set of principal color components and the reference set of principal color components indicates a correspondence between video 315 and surgical scene 125. As a counter example, at least a portion of image frames 320 of video 315 can depict environments other than surgical scene 125, such as the operating room or a different biological surface. To that end, generating principal color components and effecting the comparison as described can improve performance of example process 300 by reducing the number of image frames 320 that are erroneously processed by de-smoking operations.

As smoke 330 will generally appear whitish, the presence of smoke 330 will tend to lower the average saturation in image frames 320 of video 315. Saturation of a color, in the context of additive color mixing, is determined by a combination of intensity (color independent) and the distribution of colors across the spectrum of different wavelengths in the color space. Average saturation of color increases as wavelength distribution narrows, such that the highest saturation corresponds to a single wavelength at a high intensity, such as in monochromatic sources. In this way, an image frame including thicker smoke 330 will exhibit lower image saturation, due to a larger fraction of pixels in the image frame corresponding to the whitish smoke color.

For example, light reflecting from surfaces of surgical scene 125 that is scattered by smoke 330, and light that reflects from smoke 330 directly, will lower the average saturation relative to an image frame without smoke 330. Average saturation can also be used to differentiate between smoke-occluded frames 325 and image frames 320 for which de-smoking is less likely to be effective. For example, some tissues, such as fascia or other connective tissues, can present a whitish structural color that can be erroneously identified with smoke 330. To reduce erroneous identification of smoke occlusion, saturation thresholding can be applied to limit de-smoking operations to image frames 320 having significant smoke 330.

As such, a saturation thresholding 335 can be applied such that an average saturation above a lower saturation threshold corresponds to an image frame 320 without significant smoke 330 and an average saturation below the lower saturation threshold corresponds to smoke-occlusion. To that end, an upper threshold can be used to determine that image frame 320 is reference frame 340 by differentiating between image frames 320 without significant smoke, for which de-smoking is less effective, and reference frames 340 that include negligible or no smoke. In some embodiments, reference frame 340 is initially selected as the first image frame 320 that depicts surgical scene 125, for example, by principal component analysis or by classification using a trained ML model (e.g., convolutional neural network trained to predict whether image frame 320 represents surgical scenes 125). In this way, saturation thresholds can be defined in reference to the average saturation of reference frame 340. Replacing reference frame 340, therefore, can be based at least in part on determining that image frame 320 has an average saturation, normalized to the average saturation of reference frame 340, above 100% (e.g., greater than 1.0 in decimal notation).

Determining whether the image frame is a smoke-occluded frame 325, therefore, can include generating a comparison of the average saturation value for image frame 320 to separate image frames 320 for processing from image frames 320 to be presented without de-smoking. In an illustrative example, saturation can be described as a numerical value where 1.0 represents the average saturation of reference frame 340. In this example, therefore, a saturation threshold value can be about 0.10, about 0.20, about 0.30, about 0.40, about 0.50, about 0.60, about 0.70, about 0.80, or about 0.90, or above 1.0, including fractions and interpolations thereof. Following luminance filtering, image frames 320 having an average saturation above the upper threshold can be used as reference frames 340 and image frames 320 having an average saturation below the lower threshold can be processed as smoke-occluded frame 325, with image frames 320 having an average saturation in a threshold range between the upper threshold and the lower threshold being excluded from de-smoking operations.

It is understood that with a narrower threshold range, more image frames 320 will be classified as smoke-occluded frames 325, which increases computational resource demand of example process 300. In contrast, a wider threshold range may erroneously exclude frames including smoke 330 from processing, negatively impacting user experience. In some cases, the saturation threshold range can be from about 0.50 to about 0.80, from about 0.40 to about 0.90, from about 0.30 to about 1.0, from about 0.30 to about 1.05, from about 0.55 to about 1.05, where image frames 320 having a normalized average saturation within the threshold range being excluded from de-smoking, image frames 320 having a normalized average saturation lower than the threshold range being included in de-smoking processes, and image frames 320 having a normalized average saturation above the threshold range being used to replace reference frame 340. In some embodiments, lower threshold is 0.55, upper threshold is 1.05, and a third threshold limit of 1.10 is applied to reduce the likelihood that image frame 320 deviates from reference frame 340 too greatly (e.g., representing a scene other than surgical scene 125) and is erroneously used to replace reference frame 340.

While saturation threshold value 335 is described in terms of average saturation, the terms "above" and "below" are used in reference to a value that is higher for smoke-occluded frames 325 than for reference frames 340. As such, it is understood that a different threshold value can be defined such that the relationship is reversed, with smoke-occluded frames 325 having a value below the threshold. As described in reference to operation 309, saturation thresholding 335 can be used to distinguish between frames without smoke 330 and frames that may include smoke 330, where additional operations can be implemented to limit the frequency of de-smoking operations, as an approach to improving system performance.

In some embodiments, operation 303 can include defining a newly received image frame as reference frame 340, even when an existing reference frame 340 is already available. Advantageously, redefining reference frame 340 can improve performance of de-smoking operations of example process 300 by accounting for shifts in principal color components of surgical scene 125, for example, where the image sensor is repositioned during a surgical procedure.

In some embodiments, example process 300 includes generating a lookup table 345 using reference frame 340 at operation 305. Description of embodiments focuses on lookup tables, but it is understood that a mapping can be structured in other forms as well of which a lookup table is one example. Operation 305 can include different approaches to generating a mapping, such as generating a lookup table 345, as described in more detail in reference to FIG. 4C. Lookup table 345 can be or include a relational database describing a mapping of the color space used by image sensor 121 to a number of color bins 410 (in reference to FIGS. 4A-4C). The number of color bins 410 and the mappings from the color space to the color bins can be based at least in part on the distribution of principal colors detected in reference frame 340. In some embodiments, the lookup table includes an index or other data structure configured to map tens of millions of colors generated by a typical three-color image sensor to a reduced set of colors.

In operation, lookup table 345 can be or include an array of relations by which a set of color tuples from the color space is mapped to a bin representing a quantized color tuple from the color space, such that the color space can be quantized to a number of colors smaller than the full size of the color space. In terms of data processing, on a pixel-wise basis, quantization can include a search for a color tuple of a pixel from an image frame that returns the quantized color. To facilitate de-smoking operations, the color bins of lookup table 345 can map colors in the color space to estimated un-occluded colors in surgical scene 125, as described in more detail in reference to FIG. 5. For example, part of operations for generating lookup table 345 can include identifying principal color components of surgical scene 125 and identifying the components as the likely colors of un-occluded tissue.

In some embodiments, example process 300 includes storing lookup table 345 at operation 307. Lookup table 345 can be stored in a buffer 347 of reference frame data. Buffer 347 of reference frame data can include lookup table data from multiple reference frames 340 identified from preceding image frames 320 in video 315 (e.g., from previous iterations of example process 300). As previously described, operation 303 can include assigning a new image frame as reference frame 340 to reduce the potential influence of changes in surgical scene 125 on de-smoking operations. In an illustrative example, buffer 347 of reference frame data can be used to introduce a persistence parameter for color bins and mappings included in look up table 345, to reduce short-timescale changes in surgical scene 125 from affecting de-smoking operations and reducing the potential influence of an erroneous identification of reference frame 340.

In an illustrative example, buffer 347 of reference frame data can be used to generate a value for the extent of a change between lookup table 345 and a number of prior lookup tables, where the reference frame can be rejected if the change exceeds an allowed threshold. In some embodiments, buffer 347 can store data for about 5 or more lookup tables, about 10 or more lookup tables, about 15 or more lookup tables, about 20 or more lookup tables, about 25 or more lookup tables, about 30 or more lookup tables, about 35 or more lookup tables, about 40 or more lookup tables, about 45 or more lookup tables, about 50 or more lookup tables, about 60 or more lookup tables, about 70 or more lookup tables, about 80 or more lookup tables, about 90 or more lookup tables, about 100 or more lookup tables, about 150 or more lookup tables, about 200 or more lookup tables, or more, including fractions and interpolations thereof As data processing operations applied to buffer 347 of reference data can be implemented in parallel with other operations of example process 300, increasing the number of reference frames 340 for which lookup table data is stored in buffer 347 can have little effect on the latency introduced by de-smoking operations. Benefits of buffer 347 to reduce error introduced at operation 303 can diminish at higher buffer sizes that will include data for surgical scene 125 that can be significantly different relative to the current state of surgical scene 125 depicted in reference frame 340. In some embodiments, a size of buffer 347 can be dynamic, for example, by measuring dynamics in the change extent parameter or by tracking a number of erroneously identified reference frames. In some embodiments, buffer 347 of reference frame data can store data for 100 reference frames as an initial value and can modify the size to improve error in de-smoking operations. In this way, implementing buffer 347 of reference frame data in operation 307 can improve the robustness of example process 300 and can improve the overall performance of de-smoking operations applied to video 315.

In some embodiments, example process 300 includes determining whether image frame 320 of video 315 includes smoke 330 at operation 309. Operation 309 can be a separate operation from operation 303 where example process 300 separates saturation thresholding 335 for determining reference frame 340 from saturation thresholding 335 for determining smoke-occluded frame 325. As such, operation 309 includes determining whether image frame 320 includes smoke 330. In some embodiments, operation 309 can follow operation 303 where the image frame depicts surgical scene 125 but is not appropriate as reference frame 340 (e.g., filtered out of a high-pass saturation filter used to determine reference frames 340). In such cases, an iteration of example process 300 proceeds without operations 305 and 307, and de-smoking operations proceed using a previously generated lookup table 345 (e.g., drawn from buffer 347).

Determining that an image frame 320 is a smoke-occluded frame 325 can also include monitoring signals from components of surgical system 100-A or 100-B. In some embodiments, an activation of a cauterizing instrument (e.g., harmonic scalpel) generates a signal indicating a cauterization event that is likely to generate smoke 330 in the surgical scene 125. The signal can be a digital signal generated by the surgical system and/or can be measured electronically by measuring one or more electrical settings for the component. In response to receiving the signal, the computer system implementing example process 300 can initiate operations. To that end, video 315 can be received in a buffered video stream, such that image frames 320 corresponding to a time-period preceding receipt of the signal can be selected for use as potential reference frames 340. The time period can correspond to a number of frames through the framerate of video 315. For example, for a framerate of 120 Hz, at least one image frame 320 corresponding to 50 milliseconds preceding the signal, or six frames, can be selected for processing as a potential reference frame 340.

In some embodiments, example process 300 includes removing smoke 330 from smoke-occluded frame 325 at operation 311. As described in more detail in reference to FIG. 5, removing smoke 330 can include multiple suboperations implemented on a pixel-wise basis for at least a portion of the pixels 505 included in smoke-occluded frame 325. To that end, smoke removal can include determining an estimated true color 535 of a pixel 505 in smoke-occluded frame 325, based at least in part on an imaged color 513 of the pixel 505, a quantized imaged color 520 determined using lookup table 345 and smoke color 525. As such, estimated true color 535 can be closer to an un-occluded color of the tissue (e.g., as in reference frame 340) than imaged color 513 in the color space. As described in more detail in reference to FIG. 5, removal of smoke 330 can include normalizing imaged color 513 and other operations to estimate true color 535.

In some embodiments, operation 311 can be repeated for each pixel in smoke-occluded frame 325 but can also be implemented for a subset of pixels. For example, at least a portion of pixels of can be located in regions of image frames 320 that will not be visible on a display or are outside a region of interest of a viewer, which is typically near the center of the field of view of the image sensor 121. In this way, processing every pixel in smoke-occluded frame 325 can introduce inefficiency into example process 300 without significant added benefit. As such, example process 300 can exclude pixels from one or more regions of smoke-occluded frame 325 from operation 309, based, for example, on location in the frame (e.g., distance from the edge of the frame). In some embodiments, operation 311 can be localized in smoke-occluded frame 325 by manual indication of a user. In an illustrative embodiment, an interactive display presenting video 315 can be configured to receive a user action (e.g., a touch on a tactile display, an interaction with a peripheral input device) to manually indicate regions with smoke 330. In this way, a subset of pixels in smoke-occluded frame 325 can processed as part of operation 311, where the subset can be determined in multiple different ways to balance computational resource demand, latency, and user experience.

Figure 5:
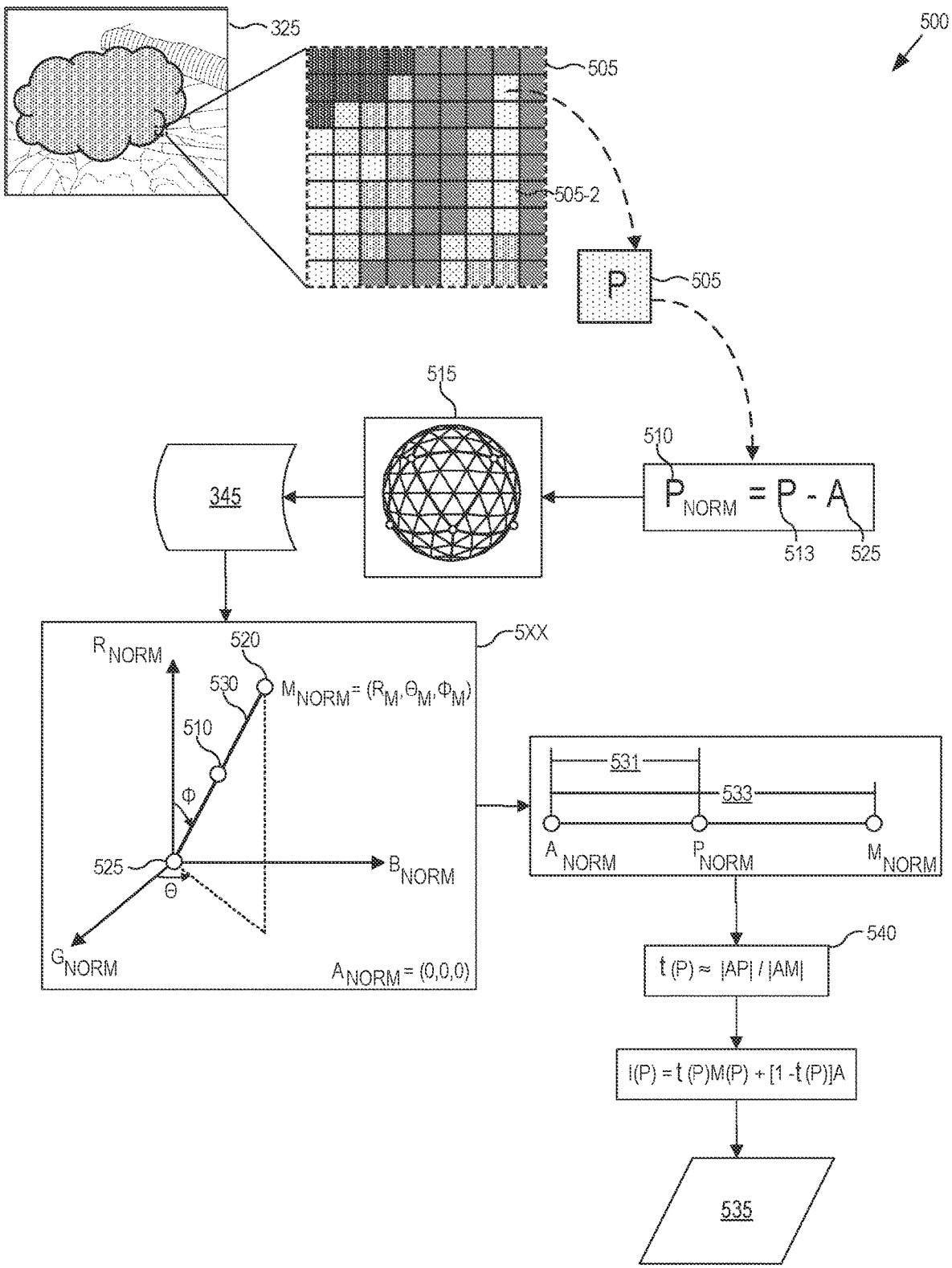
FIG. 5 is a schematic diagram illustrative an example process for determining an estimated true color of a pixel, in accordance with embodiments of the present disclosure.

In some embodiments, example process 300 includes generating a de-smoked image frame 355 including at least a subset of modified pixels as described in more detail in reference to FIG. 5, which can be processed to be reintroduced into video 315, stored as an image file, or otherwise outputted at operation 313. In some embodiments, de-smoked image frame 355 is generated by replacing imaged color 520 with estimated true color 535 for pixels processed at operation 309, which can be fewer than the total number of pixels in smoke-occluded frame 325. Generating de-smoked image frame 355 can include smoothing the de-smoked image using an edge-aware smoothing function. Edge-aware smoothing describes an image processing technique that smooths away noise or textures while retaining sharp edges. Examples include, but are not limited to median, bilateral, guided, anisotropic diffusion, and Kuwahara filters. Edge aware smoothing can be implemented to reduce high frequency information 365 that is inserted as an artifact of de-smoking, which can appear as edges, discoloration, distortion of natural tissue structures, or the like. For that reason, reduction of artifacts including high frequency information 365 can significantly improve perceived quality of de-smoked images. In contrast, artifact laden de-smoked frames 355 can be distracting to viewers and can induce a surgeon to make mistakes.

In some embodiments, operation 313 includes outputting operations, such as for generating visualization data 360 using de-smoked image frame 355. Visualization data 360 can be a structured form of de-smoked image frame 355 for presentation on a display of a surgical system (e.g., display 109 of FIG. 1A and FIG. 1B), which can include one or more image formatting operations to configure de-smoked image frame 355 for presentation on one or more types of display devices, storage in data storage devices, and/or electronic transfer over a network (e.g., as part of a video stream being distributed over the internet). Visualization data 360 can be sent to display 109 in place of the corresponding image frame 320 of video 315. For example, where video 315 is a file stored in a data store, de-smoked image frame 355 can replace the original frame in the file. In another example, where video 315 is presented as a video stream generated during a surgical procedure, visualization data 360 can be reintroduced into video 315 in place of image frame 320 in near-real time to generate a de-smoked video stream 370.

Figure 4A:
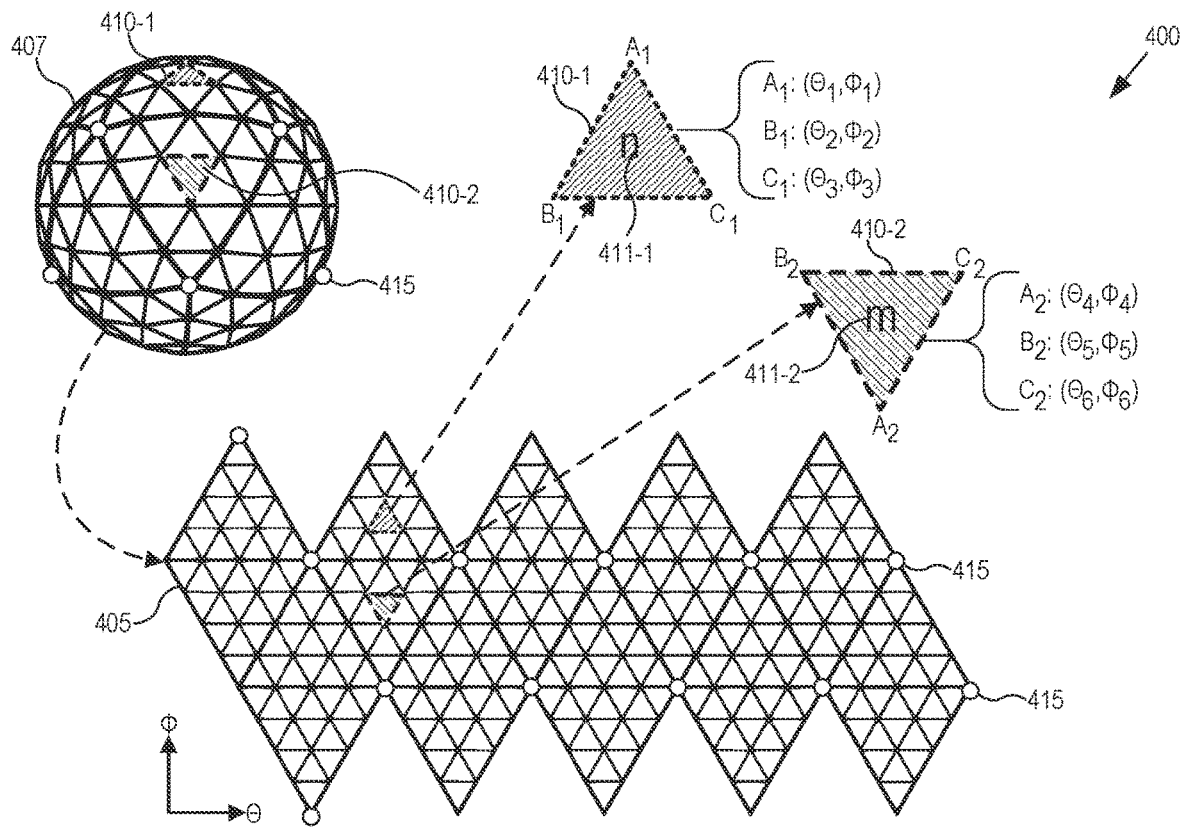
FIG. 4A is a schematic diagram illustrating an example technique for generating a mapping for color quantization, in line with embodiments of the present disclosure.

FIG. 4A is a schematic diagram illustrating an example technique 400 for generating a lookup table for color quantization, in line with embodiments of the present disclosure. Example technique 400 is illustrated diagrammatically to simplify explanation. It is understood that the visual aspects of FIG. 4A represent operations applied to image data from video, such as video 315 of FIG. 3, generated in the context described in reference to FIGS. 1A-1B. As such, example technique 400 can be applied to one or more image frames 320 of video 315, as part of operations to generate lookup tables in reference to FIG. 3 and/or to estimate smoke color 525 in reference to FIG. 5.

In some embodiments, generating a lookup table for color quantization can include operations that are implemented on a pixel-wise basis for at least a subset of pixels making up image frame 320 (e.g., reference frame 340, smoke-occluded frame 325) that include defining a spherical coordinate system 405 spanning a color space, such as the RBG color space that is commonly used by three-color image sensors. In this way, a unit sphere 407 can be defined such that each point on a surface of unit sphere 407 in the spherical coordinate system 405 corresponds to a distinct color in the color space, for which every pixel in image frame 320 can be described by a tuple of values $(r, \theta, \phi)$, where $r=1$. As previously described, an 8-bit color sensor can generate tens of millions of different colors, each described by a distinct color tuple in the color space. To reduce the computational resource demand of example process 300, the number of distinct colors included in reference frame 340 can be decreased at least in part by quantizing the spherical coordinate system 405 into a number of color bins 410, which can be uniformly distributed in the color space or non-uniformly distributed.

Colors can be quantized from tens of millions of colors down to about 1,000,000 or fewer colors, about 100,000 or fewer colors, about 50,000 or fewer colors, about 25,000 or fewer colors, about 10,000 or fewer colors, about 5,000 or fewer colors, about 1,000 or fewer colors, about 500 or fewer colors, or fewer, including fractions and interpolations thereof. Advantageously, reducing the number of colors in image frames 320 using quantization can reduce the computational resource demand of operations of example process 300 while also having negligible effect on the ability of a surgeon to interpret surgical scene 125. While human eyes are capable of discerning as many as ten million distinct colors, color quantization can have little influence on the meaning of images where (1) surgical scene 125 does not exhibit colors in one or more regions of the color space; (2) the viewer is interpreting structural or high-frequency information as well as or instead of color information; and/or (3) a lookup table preserves a number of colors high enough that the viewer can interpret surgical scene 125 accurately despite the reduced color information.

In some embodiments, quantization is implemented using lookup tables that map the color space into a set of color bins 410, which can reduce latency of operations of example process 300 by improving the computational approach to quantizing colors, relative to other techniques such as kd-tree search or k-means. Color bins 410, illustrated as triangular in shape, can assume any shape in spherical space by being defined using a number of meridians about unit sphere 407. For example, color bins 410 defined by three meridians will be triangular, while color bins 410 defined by six meridians will be hexagonal.

A first color bin 410-1 is defined by a first triad of colors $A_1B_1C_1$ on the surface of unit sphere 407. Similarly, a second color bin 410-2 is defined by a second triad of colors $A_2B_2C_2$ on the surface of unit sphere 407. First color bin 410-1 is labeled "n" and second color bin 410-2 is labeled "m" to indicate that color bins 410 map a region of the color space to a quantized color 411 that can be a centroid of a respective color bin 410, an average color of the respective color bin 410, or the like. In this way, quantization of colors in image frame 320 can include reducing colors in proportion to the area of color bins 410 in spherical coordinate system 405. With a larger number of color bins 410, more colors are preserved after quantization. With fewer color bins 410, fewer colors are preserved.

As previously described, a lookup table can be or include a computer-searchable mapping of colors falling within the boundary of a given color bin 410 to the quantized color 411, such that a color can be quantized by querying the lookup table for the corresponding coordinates in spherical coordinate system 405. Generating the searchable mapping for the lookup table can include identifying boundary coordinates for each color bin 410 and determining ranges of color coordinates in spherical space that fall within each color bin 410. Various approaches can be used to assign boundary-colors. As illustrated in FIG. 4A, nodes 415 or other boundary points in spherical coordinate system 405 can define which color bin 410 is mapped to boundary colors such that no single color is mapped to multiple bins 410.

In some embodiments, quantization can be non-uniform in spherical coordinate system 405, for example, by being informed by distributions of colors in image frames 320. Where surgical scene 125 includes relatively sparse color information in a given region of spherical coordinate system 405, the area of the corresponding color bin 405 can be enlarged to map more colors to a single quantized color 411. Similarly, where surgical scene 125 is relatively dense in a different region of spherical coordinate system 405, relatively smaller color bins 410 can be defined in the corresponding region to map relatively fewer colors to the corresponding quantized color 411.

In an illustrative example, an initial uniform size of color bins 410 can be used to sample unit sphere 407. Bin sizes can be adjusted to target computational resources on colors that carry important information for the viewer. Where surgical scene 125 includes relatively sparse information in green and yellow regions of color space, corresponding color bins 410 can be made larger. Where surgical scene 125 includes relatively rich information in red, brown, and blue regions of the color space, corresponding color bins 410 can be made smaller. Advantageously, dynamic bin 410 sizing can improve the accuracy of de-smoking operations by reducing the extent of quantization in regions of the color space that carry significant information. As de-smoking can include estimating the true color of a pixel from an assumed smoke color and an estimate of a transmission coefficient, a relatively smaller quantization can improve accuracy with a relatively small increase in computational resource demand incurred by the process of resizing color bins 410, as estimating of un-occluded color uses can proceed via a lookup table rather than quantization.

Figure 4B:
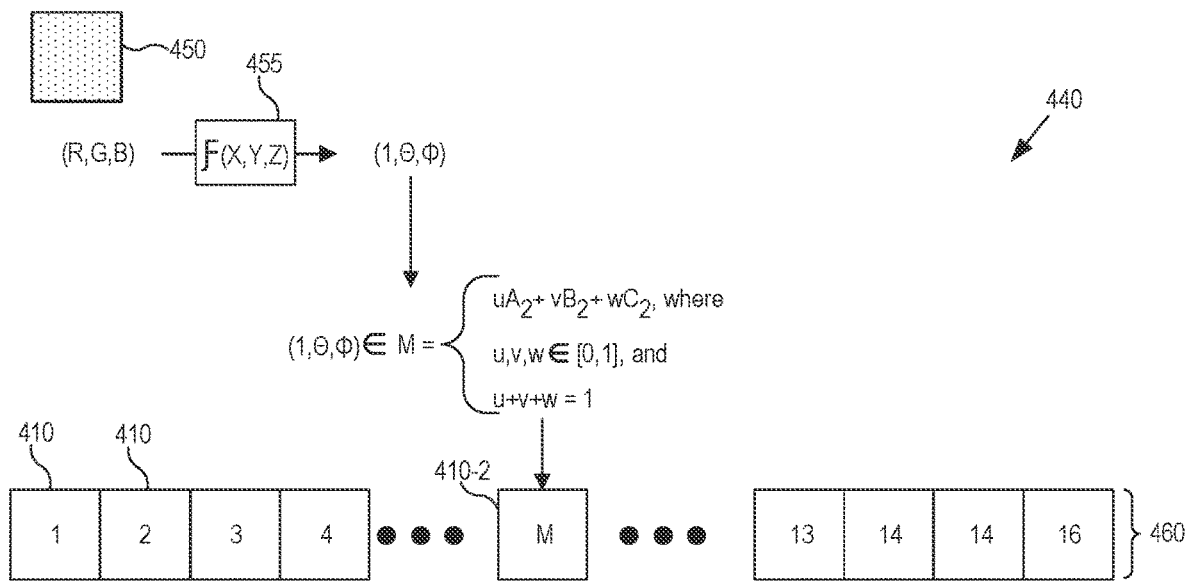
FIG. 4B is a schematic diagram illustrating an example technique 440 for quantizing a color 450, in accordance with embodiments of the present disclosure.

FIG. 4B is a schematic diagram illustrating an example technique 440 for quantizing a color 450, in accordance with embodiments of the present disclosure. In the context of populating a lookup table (e.g., lookup table 345 of FIG. 3) color 450 can be transformed 455 into spherical coordinates to correspond with spherical coordinate system 405 and mapped to a bin 410 (illustrated for second color bin 410-2 of FIG. 4B) in one or more ways. Example technique 440 illustrates an algebraic technique for assessing whether color 450 maps to second bin 420-2 by satisfying that the color tuple for color 450 in spherical coordinates is a member of a set of colors whose elements are defined as convex combinations of the three colors $A_2$, $B_2$, and $C_2$. Where color 450 ∈ M is true, color 450 is mapped to second bin 410-2.

In some embodiments, example technique 440 includes geometric approaches for mapping colors to color bins 410. For example, mappings for second color bin 410-2 can be defined for the region of unit sphere 407 corresponding to second color bin 410-2 using spherical trigonometric definitions, where colors mapped to second quantized color 411-2 are those included within the region defined by vectors $\overrightarrow{AB}$, $\overrightarrow{AC}$, and $\overrightarrow{BC}$, as would be understood by a person having ordinary skill in the art. For example, by projecting spherical coordinate system 405 onto 2D plane with φ-θ axes, sets of coordinates can be defined for each color bin 410 and the lookup table can be populated.

In some embodiments, color bins 410 are defined by uniformly sampling the surface of unit sphere 307 with a number (e.g., 1000) points, and defining a distance from each point within which a color is quantized to the color corresponding to the respective point. In such cases, overlapping regions can be decided based on whichever point is closer. As previously described, such algorithmic decisions can be made as part of generating a lookup table, such that quantization and estimation of un-occluded colors can proceed via querying the lookup table instead of searching for nearest points.

In some embodiments, each color in a color space (e.g., tens of millions of colors in an 8-bit RGB color space) is mapped to a smoke line of a set of smoke lines as an approach to reducing computational complexity and improving performance of de-smoking operations. As described in more detail in reference to FIG. 5, a smoke line is defined as a chord in spherical coordinates that connects a smoke color to an imaged color and extends to an estimated un-occluded color. In contrast to the algebraic and geometric techniques described above, mapping to a smoke line can include defining a set of smoke lines in spherical coordinate system 405. For example, unit sphere 407 can be sampled uniformly, such that each sampled point can be defined as a terminus of a smoke line. In the context of example technique 400, each quantized color can 411 can be defined using the uniform sampling. In this way, each color in the color space can be mapped to the nearest smoke line through an index of smoke lines. For example, 1000 smoke lines can be defined over spherical coordinate system 405.

Mapping a color to the nearest smoke line can include normalizing the color with respect to a smoke color, as described in more detail in reference to FIG. 5, to facilitate projecting the color onto a spherical coordinate system having the smoke color as the origin. The normalized color can then projected onto unit sphere 407 by normalizing the magnitude of the RGB tuple to one (e.g., $\sqrt{R^2+G^2+B^2}=1$), which can be accomplished by normalizing each individual color channel with respect to the maximum value for the color channels (e.g., in an 8-bit color space the minimum value is 0 and the maximum value is 256).

Mapping to the nearest smoke line can include applying a geometric nearest neighbor approach to determine the hazeline with the lowest euclidean distance for a given normalized color. Techniques can also include generating a mapping (e.g., a look up table or other index) for which each element maps a quantized RGB tuple in spherical coordinates to a smoke line of the set of smoke lines (e.g., in a reduced color set of 1000 colors rather than tens of millions). To that end, normalized colors can be quantized such that each element of an RGB tuple is mapped to a subset of values. In an illustrative example, an RGB tuple of [255, 127, 255] can be normalized by dividing by 256, giving a normalized tuple of [0.996, 0.498, 0.996]. For an example smoke color of [128, 128, 128] or [0.5, 0.5, 0.5], the normalized RGB tuple with respect to the smoke color is:

$$\frac{(1-0.5, 0.498-0.5, 1-0.5)}{\sqrt{((1-0.5)^2+(0.498-0.5)^2+(1-0.5)^2)}} = (0.7071, -0.0028, 0.7071)$$

note that, in this example, the RGB tuple was normalized with respect to the maximum 8-bit value of 255 before being normalized with respect to the smoke color. It is understood that algebraically the two operations can be transposed, where the smoke color (being an RGB tuple) is also normalized with respect to the same maximum value. To assign the RGB tuple to a smoke line, the tuple [0.7071, −0.0028, 0.7071] is quantized to an integer value (e.g., from 0 to 31 corresponding to 32 quantized values for each element of the RGB tuple corresponding to approximately 30,000 different quantized colors 411). In this illustrative example, the quantized value is [26, 15, 26] (e.g., 0.7071*16+15=26.3 and −0.0028*16+15=14.95). Finally, the quantized RGB tuple is assigned to a smoke line using a mapping of quantized colors to smoke lines (e.g., a lookup table, an index, or the like). In some embodiments, 1000 smoke lines are defined by sampling unit sphere 407, such that the RGB tuple is mapped to a smoke line from [0,999].

Figure 4C:
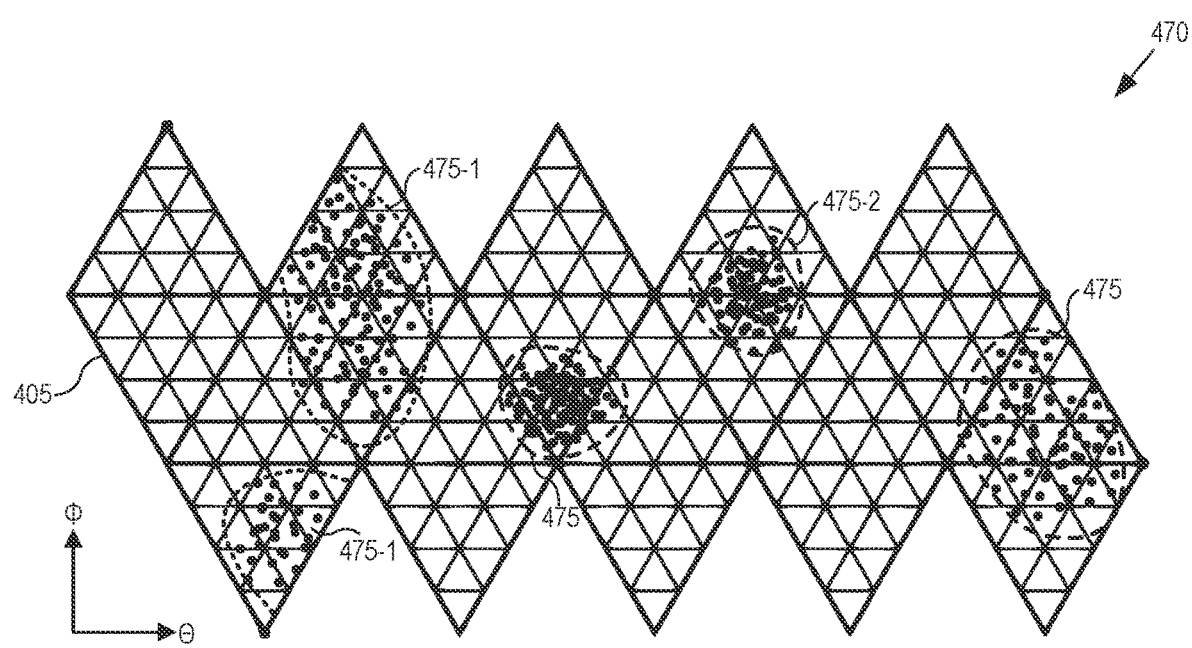
FIG. 4C is a schematic diagram illustrating an example technique 470 for determining estimated un-occluded colors of surgical scene 125, in accordance with some embodiments.

FIG. 4C is a schematic diagram illustrating an example technique 470 for determining estimated un-occluded colors of surgical scene 125, in accordance with some embodiments. Example technique 470 illustrates distributions 475 of different colors in spherical coordinate system 405. Images of surgical scene 125, being an internal surface of a body cavity, are likely to include multiple distinct distributions 475 of color in spherical coordinate system 405. In FIG. 4C, each point represents a pixel in reference frame 340, but it is understood that a full resolution image will include more points (e.g., up to and including millions of points), such that sampling may be used to reduce computational resource demand. In some embodiments, distributions 475 are quantized, as described in more detail in reference to FIGS. 4A-4B, to further reduce the number of colors used in de-smoking operations. In some embodiments, however, statistical measures including, but not limited to mean, variance, or deconvolution can be used directly on distributions 475 to determine a weighted-average color.

As illustrated, distributions 475 are not necessarily uniform. For example, a first distribution 475 can be relatively broad as a result of the convolution of multiple smaller distributions, while a second distribution 475-2 can be relatively narrow, such that a single average color can be determined. Distributions 475 that are quantized can be processed to identify principal colors to be used as estimated un-occluded color 520 (in reference to FIG. 5), with which lookup table 345 can be populated. Populating lookup table 345 can include generating histograms for each distribution 475 to which statistical methods can be applied to determine average color. Populating lookup table 345, therefore, can be understood to include mapping colors from a color space to a set of color bins 410 for which each bin corresponds to an estimated un-occluded color 520, populating a histogram for each distribution showing frequency against bin number, and determining a quantized color 411 based at least in part on population statistics.

FIG. 5 is a schematic diagram illustrating an example process 500 for determining an estimated true color 535 of a pixel 505, in accordance with embodiments of the present disclosure. Example process 500 is illustrated as a flow of operations applied to data representing an imaged color 513 of pixel 505, in reference to an estimated un-occluded color 520 and a smoke color 525. As described in more detail in reference to FIG. 3, pixel 505 can be included as one of multiple pixels 505 in smoke-occluded frame 325 of video 315. In this way, the operations of example process 500 can form a part of operation 311 of FIG. 3 for de-smoking smoke-occluded image frame 325.

Pixel 505 as generated by image sensor 121 is characterized by a color tuple that can include multiple coordinates in a color space, such as an RBG color triad typically generated by tri-color image sensors. As such, the color tuple for pixel 505 can include three different scalar values corresponding to a red component, a green component, and a blue component. Where pixel 505 is located in a region occluded by smoke 330, imaged color 513 will be a convex combination of a true color and smoke color 525 ("A"). As the true color without smoke color 525 cannot be known, estimated true color 535 of pixel 505 is found by estimating a transmission coefficient 540 ("t(P)") and assigning estimated un-occluded color 520 ("M") using lookup table 345. In some embodiments, imaged color 513 is mapped to a smoke line 530 to assign estimated un-occluded color 520, as described in more detail in reference to FIGS. 4A-4C.

To reduce the influence of smoke color 525 on transmission coefficient 540, imaged color 513 is normalized relative to smoke color 525 to generate normalized image color 510. Normalized image color 510 is transformed into spherical coordinates using a spherical coordinate system 515 having smoke color 525 as the origin. In contrast to the unit sphere 407 described in reference to FIG. 4A, spherical coordinate system 515 is specific to smoke color 525. As such, accuracy of estimated un-occluded color 520 is affected by the accuracy of smoke color 525. As described in more detail in reference to FIG. 6, de-smoking techniques described herein in reference to FIG. 3 can include operations for refining smoke color 525 from an initial assumption by using smoke-occluded frames 325 of video 315 to generate lookup tables including smoke color candidates and selecting a new smoke color 525 from amongst the candidates.

Normalized imaged color 510 in spherical coordinates can be used to query lookup table 345, to return an estimated un-occluded color 520. Together, smoke color 525 and estimated un-occluded color 520 can be plotted on a smoke line 530 between the origin in spherical coordinate system 515, corresponding to smoke color 525 and estimated un-occluded color 520. Normalized imaged color 510, being assumed to be a convex combination of smoke color 525 and estimated un-occluded color 520, will lie on or near smoke line 530.

Smoke line 530, in turn, can be used to estimate transmission coefficient 540 by defining a first distance 531 between a normalized smoke color 525 and normalized image color 510 and a second distance between smoke color 525 and estimated un-occluded color 520. Transmission coefficient 540 in turn can be estimated as the ratio of first distance 531 and second distance 533. In some embodiments, estimated true color 535 can be generated using the following expression:

$$I(P) = t(P)M(P) + [1-t(P)]A$$

where I(P) is estimated true color 535, t(P) is transmission coefficient 540, M(P) is estimated un-occluded color 520, and A is smoke color 525. As described in reference to FIG. 3, estimated true color 535 can be used to replace pixel 505 in de-smoked image frame 370. The expression above, using estimated transmission coefficient 540, produces estimated true color 535 for pixel 505. As such, example process 500 can be repeated for multiple pixels 505, up to and including each pixel of occluded image frame 325, resulting in de-smoked image frame 370 exhibiting a reduction of the smoke occlusion relative to image frame 320.

In some embodiments, as described in more detail in reference to FIG. 3, the operations of example process 500 can be applied to each pixel 505 of smoke-occluded frame 325, each smokey pixel 505 of smoke-occluded frame 325, and/or a subset of pixels 505 of smoke-occluded frame 325, as part of generating de-smoked image frame 370. In some embodiments a transmission map is generated for the smoke-occluded frame 325, where the transmission map describes a respective value of transmission coefficient 540 for each pixel 505. The transmission map, in turn, can be smoothed via an edge aware filtering method to preserve strong edges and to smooth high-frequency information more likely to result from image processing artifacts (e.g., reducing non-meaningful structural information in de-smoked image frame 370). Advantageously, such smoothing reduces or eliminates drastic changes to surgical scene 125 color while also de-smoking the smoke-occluded image frame 325 to have perceivable restoration of image quality. Additionally, smoothing permits neighboring pixels to have similar transmission values, to reduce appearance of false edges in de-smoked image frame 370. While smoothing can be inappropriate for de-hazing, de-fogging, or de-smoking wide-angle images that include long distances toward a horizon, surgical scene 125 will typically occupy smaller dimensions, such as inner spaces of body cavities, and smoke will be concentrated at a point within surgical scene 125 (e.g., the point of cauterization).

Figure 6:
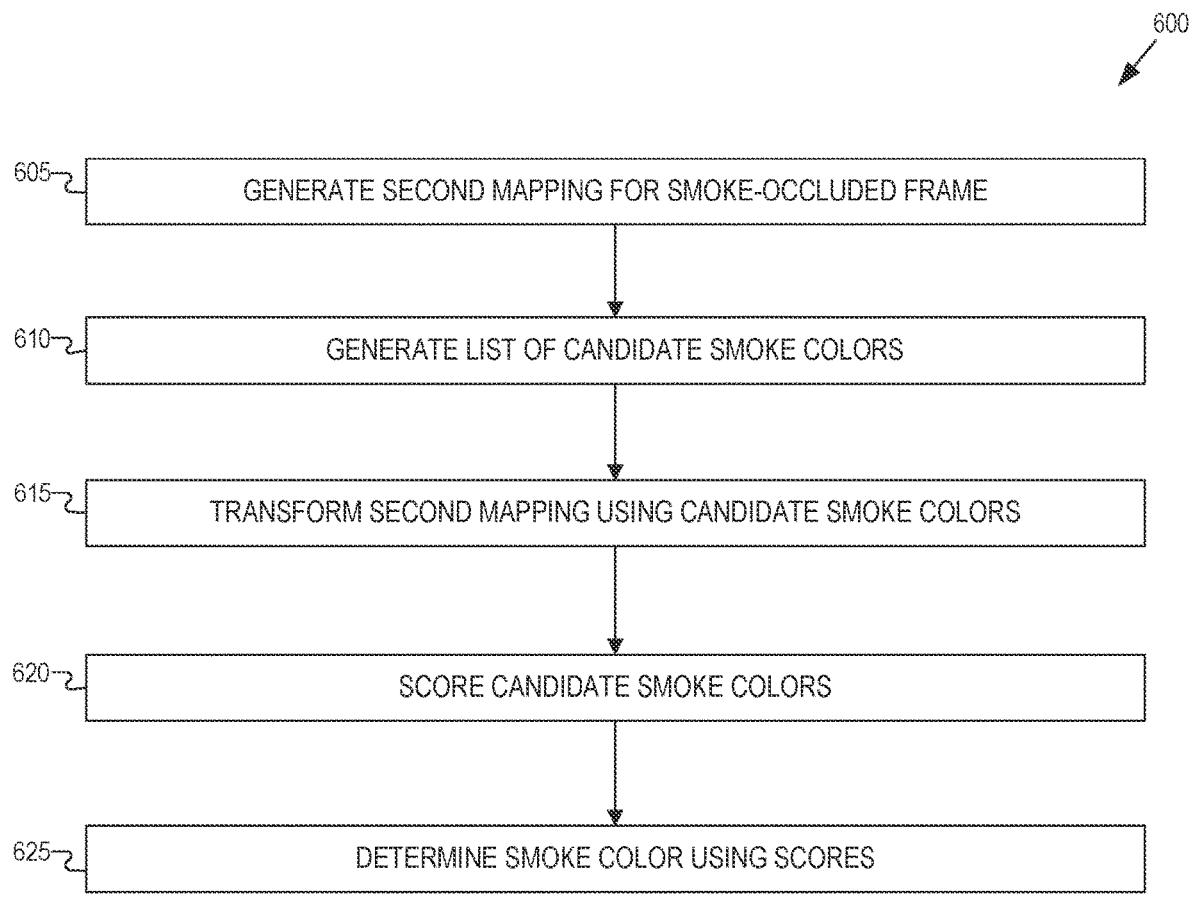
FIG. 6 is a flow chart describing an example process for refining smoke color, in accordance with embodiments of the present disclosure.

FIG. 6 is a flow chart describing an example process 600 for refining smoke color 525, in accordance with embodiments of the present disclosure. In reference to example technique 500, smoke color 525 can be assumed as a pre-determined color tuple based, for example, on prior iterations of example process 300 of FIG. 3. In some embodiments, smoke color 525 is refined and/or replaced during de-smoking of video 315 by generating a second mapping using smoke-occluded frame 325 and using the second lookup table to evaluate smoke color candidates. The operations of example process 600 are illustrated in order, but operations can be omitted, reordered, repeated, and/or executed in parallel. Operations making up example process 600 can be encoded in computer-readable instructions, as part of a computer-implemented method or as stored on a computer readable memory device. Example process 600 can be implemented as part of example process 300, for example, as part of operation 309, when a smoke-occluded frame 325 is identified.

In some embodiments, example process 600 includes generating a second mapping using smoke-occluded frame 325 at operation 605. In some embodiments, the second mapping is a lookup table, and will be described as such in subsequence paragraphs. As described in more detail in reference to FIGS. 4A-4C, generating the second lookup table can include statistical analysis of distributions 475 in spherical coordinate space 405 to determine principal colors in images, can include mapping colors in smoke-occluded frame 325 to one of a set of smoke lines using a lookup table, or the like. As such, one or more distributions 475 generated from smoke-occluded frame 325 are likely to correspond to one or more potential smoke colors 525. The second mapping therefore, will include each principal color component in reference frame 340, as well as one or more smoke colors 525.

A list of candidate smoke colors can be generated using second mapping at operation 610. The list of candidate smoke colors can be generated in a similar manner to the estimated un-occluded colors described in reference to FIG. 4C. For example, where distribution 475 corresponding to smoke colors includes multiple local maxima, deconvolution can be used to identify smoke candidates.

At operation 615, a transformation is applied to second lookup table using the candidate smoke colors. In some embodiments, the transformation can include normalizing the second lookup table by subtracting smoke candidate tuples from the color values for each bin. As imaged color can be a convex combination of smoke color and true color, normalization in this way can transform the second lookup table to be nearer to lookup table 345 for a smoke candidate that approaches the true smoke color.

Transformed second lookup table can be compared to lookup table 345, from which a score for each smoke candidate can be generated at operation 620. Scores can represent the probability that a given smoke candidate is the true smoke color. A scores can be or include a measure of error between the transformed lookup table and lookup table 345.

In some embodiments, example process 600 includes selecting a refined smoke color from the candidates with the highest scores. In some embodiments, example process 600 includes storing refined smoke color as smoke color 525 for use in de-smoking operations of example process 300. In some embodiments, a score threshold value can be used, such that the refined smoke color does not introduce error into de-smoking operations. Similarly, smoke color 525 can be included in the list of smoke candidates generated at operation 610, such that smoke color 525 is only replaced by a more suitable smoke candidate color.

In an illustrative example, one or more non-smoke frames are processed by subtracting smoke color from a quantized color space (e.g., a 32×32×32 RGB color space). Each quantized RGB tuple value can be mapped to an index value. For example, an RGB tuple value of (40, 32, 255) can correspond to an index of (5, 4, 31). Each index can correspond to an occurrence frequency of that particular color in the images. The same process of normalization, quantization, and mapping can be repeated for smoke-occluded frames. The smoke color can be found by determining a candidate smoke color with the highest correspondence between indices from smoke-occluded frames and indices from non-smoke frames, understanding that smoke can occlude many colors in the color space. An exemplary calculation is as follows: scale a quantized (e.g., 32×32×32) color map for image frame 320 such that values scale from [0, 1]. Once scaled, a candidate smoke color is subtracted and the scaled color map is mapped to a smoke line index (e.g., in a set of [0, 999] using a smoke line 530 lookup table). Each index can be described by a weight that corresponds to occurrence frequency (e.g., an integer value greater than or equal to zero). The process is repeated from smoke-occluded frames and non-smoke frames for a given candidate smoke color. In this way, the product of the weights for the smoke-occluded frame and the non-smoke frame will be a larger number if the correspondence of a given index is high and a smaller number if the correspondence is low. The product for each index is summed across all indices and the candidate color with the highest score can be used as the smoke color.

An advantage of this approach is that it improves the ability of de-smoking operations to be scope agnostic. For any given image sensor system, color correction values or light metering used by the system can be addressed implicitly by dynamically redetermining smoke color 525 in addition to redefining reference frame 340. Additionally, the color of image frames 320 depicting surgical scene 125 dynamically adapts to the presence of smoke 330 in the scene by detecting smoke 330 in image frames 320 and limiting de-smoking operations to smoke-occluded frames 320. Accordingly, the user experience in using this feature improves dramatically as the surgeon can keep the smoke reduction feature on during the entire surgical procedure without worrying about turning on different presets for non-smoke scenes versus smoke-scenes.

The processes explained above are described in terms of computer software and hardware. The techniques described can constitute machine-executable instructions embodied within a tangible or non-transitory machine (e.g., computer) readable storage medium, that when executed by a machine (e.g., controller 107) will cause the machine to perform the operations described. Additionally, the processes can be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory, machine-accessible storage medium that provides instructions that, when executed by a machine, will cause the machine to perform operations comprising:
receiving a video of a surgical scene, the video including an image frame including pixels each having a respective imaged color;
determining that the image frame includes a smoke occlusion, wherein the imaged color of the smoke occlusion combines an un-occluded color and a smoke color;
determining an estimated un-occluded color of one or more of the pixels using a mapping between a color space and a set of color bins including the estimated un-occluded color;
determining a respective estimated true color for each of the one or more pixels using the imaged color, the estimated un-occluded color, and the smoke color; and
generating a de-smoked image frame using the respective estimated true colors of the one or more pixels, the de-smoked image exhibiting a reduction of the smoke occlusion relative to the image frame,
wherein determining respective estimated true color for each of the one or more pixels comprises, for a pixel:
subtracting the smoke color from the imaged color to generate a normalized imaged color;
defining a tuple of spherical coordinates for the normalized imaged color in a spherical coordinate system having the smoke color as the origin; and
mapping the normalized imaged color to a respective estimated un-occluded color using the tuple of spherical coordinates.

2. The at least one non-transitory, machine-accessible storage medium of claim 1, wherein generating the de-smoked image frame comprises, for the normalized pixel:
determining a first distance between the normalized imaged color and the smoke color along a smoke line between the smoke color and the estimated un-occluded color in the spherical coordinate system;
determining a transmission coefficient for the pixel as the first distance relative to a second distance between the smoke color and the estimated un-occluded color; and
generating the estimated true color using the transmission coefficient, the estimated un-occluded color, and the smoke color.

3. The at least one non-transitory, machine-accessible storage medium of claim 1, wherein the image frame is a first image frame, and wherein the instructions, when executed by the machine, further cause the machine to execute operations comprising:
generating an average saturation value for a second image frame of the video;
generating a comparison of the average saturation value to an upper threshold value;
determining that the second image frame does not include surgical smoke using the comparison; and
generating the mapping using the second image frame.

4. The at least one non-transitory, one machine-accessible storage medium of claim 3, wherein generating the mapping comprises:
defining a spherical coordinate system spanning the color space, wherein each point on a surface of a unit sphere in the spherical coordinate system corresponds to a distinct color in the color space;
populating a histogram by mapping each color in the second image frame to a bin of the plurality of uniformly distributed bins; and
determining a set of estimated un-occluded colors including the estimated un-occluded color using the histogram.

5. The at least one non-transitory, one machine-accessible storage medium of claim 3, wherein the instructions, when executed by the machine, further cause the machine to execute operations comprising:
storing the mapping in a buffer of reference frame data, the buffer of reference frame data including mapping data from a plurality of reference frames preceding the second image frame in the video.

6. The at least one non-transitory, one machine-accessible storage medium of claim 1, wherein the mapping is a first mapping and wherein the instructions, when executed by the machine, further cause the machine to execute operations comprising:
generating a second mapping of the color space to a second set of color bins including the smoke color using the image frame;
determining a plurality of smoke candidates using the second mapping;
generating a plurality of scores for the plurality of smoke candidates using the second mapping, each score of the plurality of scores representing a probability that a corresponding smoke candidate of the plurality of smoke candidates is the smoke color; and
replacing the smoke color with a smoke candidate from the plurality of smoke candidates using the plurality of scores.

7. The at least one non-transitory, machine-accessible storage medium of claim 1, wherein determining that the image frame includes a smoke occlusion comprises:
generating an average luminance of the plurality of pixels of the image frame;
generating a comparison of the average luminance to a luminance threshold value; and
determining to process the image frame using the comparison.

8. The at least one non-transitory, machine-accessible storage medium of claim 7, wherein determining to process the image frame using the comparison comprises:
generating an average saturation value for the plurality of pixels;
generating a comparison of the average saturation value to a saturation threshold value;
determining that the image frame includes the smoke occlusion using the comparison.

9. The at least one non-transitory, machine-accessible storage medium of claim 1, wherein determining that the image frame includes a smoke occlusion comprises:
generating a set of principal color components using the plurality of pixels;
generating a comparison of the set of principal color components to a reference set of principal color components of a biological surface; and
determining to process the image frame using the comparison.

10. The at least one non-transitory, machine-accessible storage medium of claim 1, wherein generating the de-smoked image frame comprises smoothing the de-smoked image using an edge-aware smoothing function.

11. The at least one non-transitory, one machine-accessible storage medium of claim 1, wherein the instructions, when executed by the machine, further cause the machine to execute operations comprising:

generating visualization data for a display in communication with the machine using the de-smoked image frame; and sending the visualization data to the display in place of the image frame in the video.

12. The at least one non-transitory, machine-accessible storage medium of claim 1, wherein the video is a video stream, and wherein the machine executes the operations in near-real time.

13. A computer-implemented method, comprising:

receiving a video of a surgical scene, the video including an image frame including pixels each having a respective imaged color;

determining that the image frame includes a smoke occlusion, wherein the imaged color of the smoke occlusion combines an un-occluded color and a smoke color;

determining an estimated un-occluded color of one or more of the pixels using a mapping between a color space and a set of color bins including the estimated un-occluded color;

determining a respective estimated true color for each of the one or more pixels using the imaged color, the estimated un-occluded color, and the smoke color; and generating a de-smoked image frame using the respective estimated true colors of the one or more pixels, the de-smoked image exhibiting a reduction of the smoke occlusion relative to the image frame, wherein determining the respective estimated true color for each of the one or more pixels comprises, for a pixel:

subtracting the smoke color from the imaged color to generate a normalized imaged color;

defining a tuple of spherical coordinates for the normalized imaged color in a spherical coordinate system having the smoke color as the origin; and mapping the normalized imaged color to a respective estimated un-occluded color using the tuple of spherical coordinates.

14. The computer-implemented method of claim 13, wherein generating the de-smoked image frame comprises, for the normalized pixel:

determining a first distance between the normalized imaged color and the smoke color along a smoke line between the smoke color and the estimated un-occluded color in the spherical coordinate system;

determining a transmission coefficient for the pixel as the first distance relative to a second distance between the smoke color and the estimated un-occluded color; and generating the estimated true color using the transmission coefficient, the estimated un-occluded color, and the smoke color.

15. The computer-implemented method of claim 13, wherein the image frame is a first image frame, the method further comprising:

generating an average saturation value for a second image frame of the video;

generating a comparison of the average saturation value to an upper threshold value;

determining that the second image frame does not include surgical smoke using the comparison; and generating the mapping using the second image frame.

16. The computer-implemented method of claim 13, wherein the mapping is a first mapping, the method further comprising:

generating a second mapping of the color space to a second set of color bins including the smoke color using the image frame;

determining a plurality of smoke candidates using the second mapping;

generating a plurality of scores for the plurality of smoke candidates using the second mapping, each score of the plurality of scores representing a probability that a corresponding smoke candidate of the plurality of smoke candidates is the smoke color; and replacing the smoke color with a smoke candidate from the plurality of smoke candidates using the plurality of scores.

17. The computer-implemented method of claim 13, wherein determining that the image frame includes a smoke occlusion due comprises:

generating an average luminance of the plurality of pixels of the image frame;

generating a comparison of the average luminance to a luminance threshold value; and determining to process the image frame using the comparison.

18. The computer-implemented method of claim 13, wherein determining to process the image frame comprises:

generating a set of principal color components using the plurality of pixels;

generating a comparison of the set of principal color components to a reference set of principal color components of a biological surface; and determining to process the image frame using the comparison.

19. At least one non-transitory, machine-accessible storage medium that provides instructions that, when executed by a machine, will cause the machine to perform operations comprising:

receiving a video of a surgical scene, the video including an image frame including pixels each having a respective imaged color;

determining that the image frame includes a smoke occlusion, wherein the imaged color of the smoke occlusion combines an un-occluded color and a smoke color;

determining an estimated un-occluded color of one or more of the pixels using a mapping between a color space and a set of color bins including the estimated un-occluded color;

determining a respective estimated true color for each of the one or more pixels using the imaged color, the estimated un-occluded color, and the smoke color; and generating a de-smoked image frame using the respective estimated true colors of the one or more pixels, the de-smoked image exhibiting a reduction of the smoke occlusion relative to the image frame, wherein the image frame is a first image frame, and wherein the instructions, when executed by the machine, further cause the machine to execute operations comprising:

generating an average saturation value for a second image frame of the video;

generating a comparison of the average saturation value to an upper threshold value;

determining that the second image frame does not include surgical smoke using the comparison; and generating the mapping using the second image frame.

* * * * *